(12) United States Patent
Elwood et al.

(10) Patent No.: US 12,048,554 B2
(45) Date of Patent: Jul. 30, 2024

(54) EEG RECORDING AND ANALYSIS

(71) Applicant: Epitel, Inc., Salt Lake City, UT (US)

(72) Inventors: Michael K. Elwood, Farmington, UT (US); Mitchell A. Frankel, Salt Lake City, UT (US); Mark J. Lehmkuhle, Salt Lake City, UT (US); Jean M. Wheeler, Salt Lake City, UT (US); Robert Lingstuyl, Salt Lake City, UT (US); Erin M. West, Midvale, UT (US); Tyler D. McGrath, Salt Lake City, UT (US)

(73) Assignee: Epitel, Inc., Salt Lake City, UT (US)

( * ) Notice: Subject to any disclaimer, the term of this patent is extended or adjusted under 35 U.S.C. 154(b) by 0 days.

(21) Appl. No.: 17/861,080

(22) Filed: Jul. 8, 2022

(65) Prior Publication Data
US 2022/0338793 A1 Oct. 27, 2022

Related U.S. Application Data

(63) Continuation of application No. 17/013,811, filed on Sep. 14, 2020.

(60) Provisional application No. 63/005,405, filed on Apr. 5, 2020.

(51) Int. Cl.
| | |
|---|---|
| *A61B 5/00* | (2006.01) |
| *A61B 5/291* | (2021.01) |
| *A61B 5/372* | (2021.01) |
| *A61B 5/374* | (2021.01) |

(Continued)

(52) U.S. Cl.
CPC .......... *A61B 5/4094* (2013.01); *A61B 5/0006* (2013.01); *A61B 5/291* (2021.01); *A61B 5/372* (2021.01); *A61B 5/374* (2021.01); *A61B 5/384* (2021.01); *A61B 5/6814* (2013.01); *A61B 5/7264* (2013.01); *A61B 5/742* (2013.01); *G06N 20/00* (2019.01)

(58) Field of Classification Search
None
See application file for complete search history.

(56) References Cited

U.S. PATENT DOCUMENTS

| | | |
|---|---|---|
| 4,936,306 A | 6/1990 | Doty |
| 5,309,923 A | 5/1994 | Leuchter et al. |
| 5,483,967 A | 1/1996 | Ohtake |

(Continued)

FOREIGN PATENT DOCUMENTS

| | | |
|---|---|---|
| EP | 2526859 A1 | 11/2012 |
| EP | 2782499 B1 | 3/2021 |

(Continued)

OTHER PUBLICATIONS

Rodriquez, K, International Search Report, PCT/US21/25489, USPTO, 8 pages, Jul. 16, 2021.

(Continued)

*Primary Examiner* — Michael R Bloch
(74) *Attorney, Agent, or Firm* — Knobbe, Martens, Olson & Bear, LLP

(57) ABSTRACT

One embodiment provides a method, including: obtaining EEG data from one or more single channel EEG sensor worn by a user; classifying, using a processor, the EEG data as one of nominal and abnormal; and providing an indication associated with a classification of the EEG data. Other embodiments are described and claimed.

21 Claims, 8 Drawing Sheets

(51) Int. Cl.
*A61B 5/384* (2021.01)
*G06N 20/00* (2019.01)

(56) References Cited

U.S. PATENT DOCUMENTS

| | | | |
|---|---|---|---|
| 5,755,230 A | 5/1998 | Schmidt et al. | |
| 6,117,077 A | 9/2000 | Del Mar et al. | |
| 6,416,471 B1* | 7/2002 | Kumar | A61B 5/0022 |
| | | | 128/903 |
| 6,473,639 B1 | 10/2002 | Fischell et al. | |
| 6,496,724 B1 | 12/2002 | Levendowski | |
| 6,735,467 B2 | 5/2004 | Wilson | |
| 7,848,794 B2 | 12/2010 | Genger et al. | |
| 7,885,706 B2 | 2/2011 | Ludvig et al. | |
| 7,970,450 B2 | 6/2011 | Kroecker et al. | |
| 8,204,583 B2 | 6/2012 | Sackellares et al. | |
| 8,538,512 B1 | 9/2013 | Bibian et al. | |
| 8,562,523 B2 | 10/2013 | Osorio | |
| 8,594,763 B1 | 11/2013 | Bibian et al. | |
| 8,626,261 B2 | 1/2014 | Ko et al. | |
| 8,628,462 B2 | 1/2014 | Berka et al. | |
| 8,666,484 B2 | 3/2014 | Nierenberg | |
| 8,688,209 B2 | 4/2014 | Verbitskiy | |
| 8,786,624 B2 | 7/2014 | Echauz et al. | |
| 8,805,527 B2 | 8/2014 | Mumford et al. | |
| 8,818,481 B2 | 8/2014 | Bly et al. | |
| 8,849,390 B2 | 9/2014 | Echauz et al. | |
| 8,868,172 B2 | 10/2014 | Leyde | |
| 8,870,764 B2 | 10/2014 | Rubin | |
| 9,186,083 B2 | 11/2015 | Osvath | |
| 9,241,649 B2 | 1/2016 | Kumar et al. | |
| 9,439,599 B2 | 9/2016 | Thompson et al. | |
| 9,459,089 B2 | 10/2016 | Ganton et al. | |
| 10,206,591 B2 | 2/2019 | Osorio | |
| 10,285,646 B1 | 5/2019 | Grant et al. | |
| 10,342,451 B2 | 7/2019 | Girouard et al. | |
| 10,448,839 B2 | 10/2019 | Shivkumar | |
| 10,463,270 B2 | 11/2019 | Leyde | |
| 10,571,541 B2 | 2/2020 | Grodzki | |
| 10,736,525 B2 | 8/2020 | Cardenas et al. | |
| 10,743,809 B1 | 8/2020 | Kamousi | |
| 10,929,753 B1 | 2/2021 | Nierenberg et al. | |
| 10,980,469 B2 | 4/2021 | Girouard et al. | |
| 10,986,465 B2 | 4/2021 | Patel et al. | |
| 11,020,035 B2 | 6/2021 | Dudek et al. | |
| 11,026,628 B1 | 6/2021 | Bruinsma et al. | |
| 11,160,505 B2 | 11/2021 | Gunasekar et al. | |
| 11,633,139 B2 | 4/2023 | Dudek et al. | |
| 11,633,144 B2 | 4/2023 | Elwood et al. | |
| 11,638,551 B2 | 5/2023 | Elwood et al. | |
| 11,779,262 B2 | 10/2023 | Elwood et al. | |
| 11,786,167 B2 | 10/2023 | Elwood et al. | |
| 11,857,330 B1 | 1/2024 | Frankel et al. | |
| 11,918,368 B1 | 3/2024 | Frankel et al. | |
| 2002/0013565 A1 | 1/2002 | Cinelli et al. | |
| 2002/0035338 A1 | 3/2002 | Dear et al. | |
| 2002/0103512 A1 | 8/2002 | Echauz et al. | |
| 2002/0109621 A1 | 8/2002 | Khair et al. | |
| 2002/0188216 A1 | 12/2002 | Kayyali et al. | |
| 2003/0074033 A1* | 4/2003 | Pless | G16H 40/60 |
| | | | 607/48 |
| 2003/0135128 A1 | 7/2003 | Suffin et al. | |
| 2003/0195429 A1 | 10/2003 | Wilson | |
| 2004/0068199 A1 | 4/2004 | Echauz et al. | |
| 2004/0079372 A1 | 4/2004 | John et al. | |
| 2005/0165323 A1* | 7/2005 | Montgomery | A61B 5/369 |
| | | | 128/903 |
| 2005/0261559 A1 | 11/2005 | Mumford et al. | |
| 2006/0111644 A1* | 5/2006 | Guttag | A61B 5/7267 |
| | | | 600/544 |
| 2007/0032733 A1 | 2/2007 | Burton | |
| 2007/0032737 A1 | 2/2007 | Causevic et al. | |
| 2007/0100666 A1 | 5/2007 | Stivoric et al. | |
| 2007/0249952 A1 | 10/2007 | Rubin et al. | |
| 2007/0270678 A1 | 11/2007 | Fadem et al. | |
| 2008/0082019 A1* | 4/2008 | Ludving | A61B 5/6814 |
| | | | 600/544 |
| 2008/0082020 A1 | 4/2008 | Collura | |
| 2008/0091089 A1 | 4/2008 | Guillory et al. | |
| 2008/0091090 A1 | 4/2008 | Guillory et al. | |
| 2008/0125669 A1 | 5/2008 | Suffin et al. | |
| 2008/0146958 A1 | 6/2008 | Guillory et al. | |
| 2008/0208008 A1 | 8/2008 | Turner | |
| 2008/0243022 A1 | 10/2008 | Donnett et al. | |
| 2008/0275327 A1 | 11/2008 | Faarbaek et al. | |
| 2008/0294031 A1 | 11/2008 | Wilson et al. | |
| 2008/0319277 A1 | 12/2008 | Bradley | |
| 2009/0054737 A1 | 2/2009 | Magar et al. | |
| 2009/0124923 A1 | 4/2009 | Sackellares et al. | |
| 2009/0137923 A1 | 5/2009 | Suffin et al. | |
| 2009/0157662 A1 | 6/2009 | Suffin et al. | |
| 2010/0143256 A1 | 6/2010 | Suffin et al. | |
| 2010/0145217 A1* | 6/2010 | Otto | A61B 5/7225 |
| | | | 324/123 R |
| 2010/0168603 A1 | 7/2010 | Himes et al. | |
| 2010/0222686 A1 | 9/2010 | Fisher et al. | |
| 2010/0234697 A1 | 9/2010 | Walter et al. | |
| 2010/0298735 A1 | 11/2010 | Suffin | |
| 2011/0015495 A1 | 1/2011 | Dothie et al. | |
| 2011/0098593 A1 | 4/2011 | Low et al. | |
| 2011/0218820 A1 | 9/2011 | Himes et al. | |
| 2011/0221590 A1 | 9/2011 | Baker et al. | |
| 2011/0279963 A1 | 11/2011 | Kumar et al. | |
| 2012/0003933 A1 | 1/2012 | Baker et al. | |
| 2012/0035451 A1 | 2/2012 | Jaffe et al. | |
| 2012/0179062 A1 | 7/2012 | Wilson | |
| 2012/0209102 A1 | 8/2012 | Ylotalo et al. | |
| 2012/0253163 A1 | 10/2012 | Afanasewicz et al. | |
| 2012/0310070 A1 | 12/2012 | Kumar et al. | |
| 2012/0330125 A1 | 12/2012 | Wilson et al. | |
| 2013/0012830 A1 | 1/2013 | Leininger et al. | |
| 2013/0310676 A1 | 11/2013 | Jung | |
| 2013/0318546 A1 | 11/2013 | Kothuri et al. | |
| 2013/0338473 A1 | 12/2013 | Bohorquez et al. | |
| 2014/0012151 A1 | 1/2014 | Nierenberg et al. | |
| 2014/0012509 A1 | 1/2014 | Barber | |
| 2014/0051044 A1 | 2/2014 | Badower et al. | |
| 2014/0121557 A1 | 5/2014 | Gannon et al. | |
| 2014/0148872 A1 | 5/2014 | Goldwasser et al. | |
| 2014/0206975 A1 | 7/2014 | Lang | |
| 2014/0206977 A1 | 7/2014 | Bahney et al. | |
| 2014/0210627 A1 | 7/2014 | Nothacker et al. | |
| 2014/0247058 A1 | 9/2014 | Mortara | |
| 2014/0313052 A1 | 10/2014 | Yarger et al. | |
| 2015/0038870 A1 | 2/2015 | Yoo et al. | |
| 2015/0088024 A1 | 3/2015 | Sackellares et al. | |
| 2015/0134580 A1 | 5/2015 | Wilson | |
| 2015/0142082 A1 | 5/2015 | Simon et al. | |
| 2015/0150505 A1 | 6/2015 | Kaskoun et al. | |
| 2015/0216436 A1 | 8/2015 | Bosl et al. | |
| 2015/0289814 A1 | 10/2015 | Magar et al. | |
| 2015/0351690 A1 | 12/2015 | Toth et al. | |
| 2015/0374255 A1 | 12/2015 | Vasapollo | |
| 2016/0000382 A1 | 1/2016 | Jain et al. | |
| 2016/0022161 A1 | 1/2016 | Khair | |
| 2016/0029958 A1 | 2/2016 | Le et al. | |
| 2016/0089049 A1 | 3/2016 | Hung et al. | |
| 2016/0256111 A1 | 9/2016 | Cheng et al. | |
| 2016/0270679 A1* | 9/2016 | Mahon | A61B 5/4047 |
| 2016/0287127 A1 | 10/2016 | Kesinger et al. | |
| 2016/0374583 A1 | 12/2016 | Cerruti et al. | |
| 2017/0055896 A1 | 3/2017 | Al-Ali et al. | |
| 2017/0076217 A1 | 3/2017 | Krumm | |
| 2017/0085000 A1 | 3/2017 | Girard | |
| 2017/0095176 A1 | 4/2017 | Sun et al. | |
| 2017/0156622 A1 | 6/2017 | Mahoor et al. | |
| 2017/0169128 A1 | 6/2017 | Batchu et al. | |
| 2017/0172414 A1 | 6/2017 | Nierenberg et al. | |
| 2017/0196456 A1 | 7/2017 | Hwang et al. | |
| 2017/0215759 A1* | 8/2017 | Dudek | A61B 5/0006 |
| 2017/0264792 A1 | 9/2017 | Lee et al. | |
| 2017/0296083 A1 | 10/2017 | Cardenas et al. | |
| 2018/0085000 A1 | 3/2018 | Weffers-Albu et al. | |
| 2018/0101656 A1 | 4/2018 | Milevski et al. | |

(56) References Cited

U.S. PATENT DOCUMENTS

| | | |
|---|---|---|
| 2018/0110466 A1 | 4/2018 | Ralston |
| 2018/0189678 A1 | 7/2018 | Gupta et al. |
| 2018/0206776 A1 | 7/2018 | Nogueira |
| 2018/0353084 A1 | 12/2018 | Wainright et al. |
| 2019/0059770 A1* | 2/2019 | Gunasekar ........... A61B 5/7435 |
| 2019/0126033 A1 | 5/2019 | Pradeep |
| 2019/0371478 A1* | 12/2019 | Rondoni ................ G16H 10/20 |
| 2019/0380583 A1 | 12/2019 | Danneels et al. |
| 2020/0022603 A1 | 1/2020 | Cardenas et al. |
| 2020/0163629 A1 | 5/2020 | Dearing et al. |
| 2020/0229706 A1 | 7/2020 | Nishimura et al. |
| 2020/0237248 A1 | 7/2020 | Willis et al. |
| 2020/0315537 A1 | 10/2020 | Magar |
| 2021/0169417 A1 | 6/2021 | Burton |
| 2021/0220064 A1 | 7/2021 | Kottenstette et al. |
| 2021/0244335 A1 | 8/2021 | Dudek et al. |
| 2021/0282701 A1 | 9/2021 | Chan et al. |
| 2021/0307672 A1 | 10/2021 | Elwood et al. |
| 2021/0353224 A1 | 11/2021 | Etkin et al. |
| 2021/0375480 A1 | 12/2021 | Mahon et al. |
| 2022/0031248 A1 | 2/2022 | Grant et al. |
| 2022/0039720 A1 | 2/2022 | Abercrombie, II et al. |
| 2022/0071547 A1 | 3/2022 | Revels et al. |
| 2022/0338780 A1 | 10/2022 | Dudek et al. |
| 2022/0338789 A1 | 10/2022 | Elwood et al. |
| 2022/0338790 A1 | 10/2022 | Elwood et al. |
| 2022/0338791 A1 | 10/2022 | Elwood et al. |
| 2022/0338792 A1 | 10/2022 | Elwood et al. |
| 2022/0346695 A1 | 11/2022 | Elwood et al. |
| 2022/0346700 A1 | 11/2022 | Elwood et al. |
| 2023/0255541 A1 | 8/2023 | Elwood et al. |
| 2023/0404471 A1 | 12/2023 | Elwood et al. |

FOREIGN PATENT DOCUMENTS

| | | |
|---|---|---|
| JP | 2010527709 A | 8/2010 |
| KR | 20170083217 A | 7/2017 |
| WO | WO 2005/109334 A2 | 11/2005 |
| WO | WO 2010/107928 A2 | 9/2010 |
| WO | WO 2015/055156 A1 | 4/2015 |
| WO | WO 2018/013569 A1 | 1/2018 |
| WO | WO 2018/218174 A1 | 11/2018 |
| WO | WO 2019/046799 A1 | 3/2019 |
| WO | WO 2022/228668 A1 | 11/2022 |

OTHER PUBLICATIONS

Jia et al. Design of a Wireless EEG System for Point-of-Care Applications Proc IEEE Annu Northeast Bioeng Conf. Apr. 2013; 2013: 78-79. (Year: 2013).

Lnggi Ramadhani Dwi Saputro et al. 2019 J. Phys.: Conf. Ser. 1201 012065 Seizure Type Classification on EEG Signal using Support Vector Machine (Year: 2019).

Rodriquez, K, International Search Report and Written Opinion, PCT/US21/25489, USPTO, 10 pages, Jul. 16, 2021.

Prabhu K.M.M., Window Functions and Their Applications in Signal Processing. ISBN-13:978-1-4665-1583-3; Taylor & Francis; 2014; in 405 pages.

INTERAXON Inc., MUSE—The Brain Sensing Headband (Technical Specification, Validation, and Research Use), Jul. 23, 2023; 1-6 pages; retrieved from the Internet: URL: https://www.eegsales.com/Shared/images/General%20Use/PDF%20Files/Muse_Technical_Specs.pdf.

European Extended Search Report dated Feb. 20, 2024 for Application No. 21784884.5 in 14 pages.

Ren K., "What You Need to Know About Periodic Advertising Sync Transfer". Bluetooth Low Energy, Broadcast, Connected Device, Location Services; Feb. 28, 2019; 4 pages.

Vandecasteele et al., "Visual Seizure Annotation and Automated Seizure Detection Using Behind-the-ear electroencephalographic Channels". Epilepsia. Apr. 2020;61(4): 766-775.

Partial Supplementary European Search Report dated Nov. 2, 2023 for Application No. 21784884.5 in 14 pages.

* cited by examiner

EEG RECORDING AND ANALYSIS

CROSS-REFERENCE TO RELATED APPLICATIONS

This application claims priority to U.S. patent application Ser. No. 17/019,811 filed Sep. 14, 2020, which in turn claims priority to U.S. provisional patent application Ser. No. 63/005,405, filed on Apr. 5, 2020 and having the same title, the contents of each of which are incorporated by reference in their entirety herein.

STATEMENT REGARDING FEDERALLY SPONSORED R&D

This invention was made with Government support under Grant No. R43NS100235, awarded by the National Institutes of Health. The Government has certain rights in the invention.

BACKGROUND

There are thousands of hospitals across the U.S. Many of these hospitals are community or rural hospitals. These community or rural hospitals conventionally are part of a hospital system or network. An example of one such network includes several community hospitals with one major tertiary hospital. A community or rural hospital outside of any large hospital network would typically contract with a large tertiary hospital for emergent and intensive-care solutions outside of the areas of expertise of the community or rural hospital.

Electroencephalogram (EEG) monitoring is conventionally only available in the large tertiary hospitals that support a neurology department with an EEG service. Many hospitals do not offer EEG monitoring. These hospitals make arrangements with larger tertiary hospitals or their partners when such monitoring is required or desirable for patients. This conventionally takes the form of a referral of the patient to the tertiary hospital for expert of specialist services. Often this includes travel or transport of the patient to the tertiary hospital for services.

BRIEF SUMMARY

In summary, one embodiment provides a method, comprising: obtaining EEG data from one or more single-channel EEG sensor worn by a user; classifying, using a processor, the EEG data as one of nominal and abnormal; and providing an indication associated with a classification of the EEG data.

Another embodiment provides a system, comprising: an output device; a processor operatively coupled to the output device; and a memory storing instructions executable by the processor to: obtain EEG data from one or more single-channel EEG sensor worn by a user; classify the EEG data as one of nominal and abnormal; and provide an indication associated with a classification of the EEG data.

A further embodiment provides a method, comprising: obtaining EEG data from two or more single channel EEG sensors worn by a user; transmitting the EEG data to a remote device; and providing, from the remote device to a display associated with a remote user, data comprising a montage of the EEG data.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, in conjunction with the accompanying drawings.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the claims, but is merely representative of those embodiments.

To optimize treatment following initial seizure diagnosis, epileptologists would ideally obtain high-quality, long-term EEG studies in the hospital with 19+-channel, wired EEG arrangement in the standard international '10-20' system. Such studies can be difficult to perform because the process is prohibitively expensive, time consuming, and extremely inconvenient for patients. Additionally, the time spent in the epilepsy monitoring unit may not capture any or all seizure activity that a person normally has over long periods of time. However, optimal treatment often depends upon identifying the full extent of a patient's convulsive (clinical) and non-convulsive (sub-clinical) seizure activity. Currently a technique for collecting seizure activity history outside of the hospital is the seizure diary—a home based, self-reported record that may be incomplete. Seizure diaries can be difficult to maintain accurately, and the diary can be inaccurate, making clinical decisions on appropriate pharmacological treatment difficult. Further, conventional EEG techniques do not adequately address the need for monitoring in many emergent care scenarios, particularly those encountered by emergency responders or clinicians in small or rural hospitals.

Turning now to the figures, representative example embodiments are described to provide a better understanding of the appended claims.

Figure 1A:
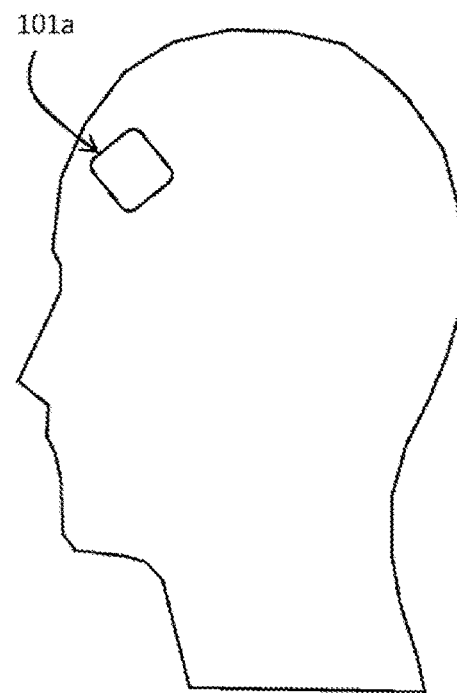
FIG. 1A illustrates an example sensor.

Referring to FIG. 1A, an embodiment provides a sensor 101a. The sensor 101a may take a variety of forms; however, the example of FIG. 1A shows a wearable sensor that adheres to the skin of a patient. The sensor 101a may include a data analytics platform that takes EEG monitoring out of the hospital. The sensor 101a features a small size and can be located in a variety of positions, reducing the burden on the user during prolonged wear. This permits EEG data collection using a small, convenient sensor 101a that provides real-time EEG data capture, as shown in FIG. 1A. This is in contrast to a complex wired electrode arrangement typically used in a hospital setting featuring many electrodes and measurement locations.

In an example shown in FIG. 1A, a small, connected health-wearable sensor 101a provides for sensing single-channel EEG data that can be analyzed for occurrences of both convulsive (clinical) and non-convulsive (subclinical) seizures. The sensor 101a senses EEG data of the user by detecting electrical activity of the brain, e.g., by sensing voltage differentials between two electrode contacts. The sensor may include two electrodes that are separated by the sensor housing, forming a single bipolar channel ("single channel") of a typical EEG montage. In an embodiment, the sensor 101a is a single-channel differentially-amplified transmitter and data logger with 6 mm diameter gold electrodes and 18 mm electrode spacing, similar to a bipolar pair in high-density EEG. The electrode contacts may be located on the surface of the device that is placed on the skin of the patient, e.g., adhered to the patient via a sticker or other adhesive that includes material such as hydrogel permitting voltage sensing. The sensor 101a is located at an appropriate place on the user, e.g., on the scalp below the hairline, in order to sense and record the single channel EEG data. The EEG data may be analyzed on-board, e.g., via application of an analysis or machine learning model stored in the sensor 101a or may be analyzed by a local device or remote device or a combination of the foregoing. By way of example, the sensor 101a may communicate through a wireless network, e.g. secure BLUETOOTH Low Energy (BLE), to a local device using a personal area network (PAN), such as communicating data to a smartphone or a tablet. Similarly, the sensor 101a may communicate with a remote device using a wide area network (WAN), such as communicating EEG data to a remote server or cloud device over the Internet, with or without communicating via an intermediary device such as a local device.

In an embodiment, an EEG monitoring sensor 101a is a self-contained recording patch including a first electrode and a second electrode, where the first and second electrodes cooperate to measure a voltage. The sensor 101a includes circuitry for generating an EEG signal from the measured voltage, amplifying the EEG signal, digitizing the EEG signal, and retrievably storing the EEG data in a memory. The sensor 101a may also include a power source and an enclosure that houses the circuitry, the power source, as well as the first and second electrodes, in a unitary package. The sensor 101a may be worn on the scalp, e.g., forehead or bi-parietal region, of the user to capture EEG data over a long period as the user goes about his or her regular, daily activities.

Figure 1B:
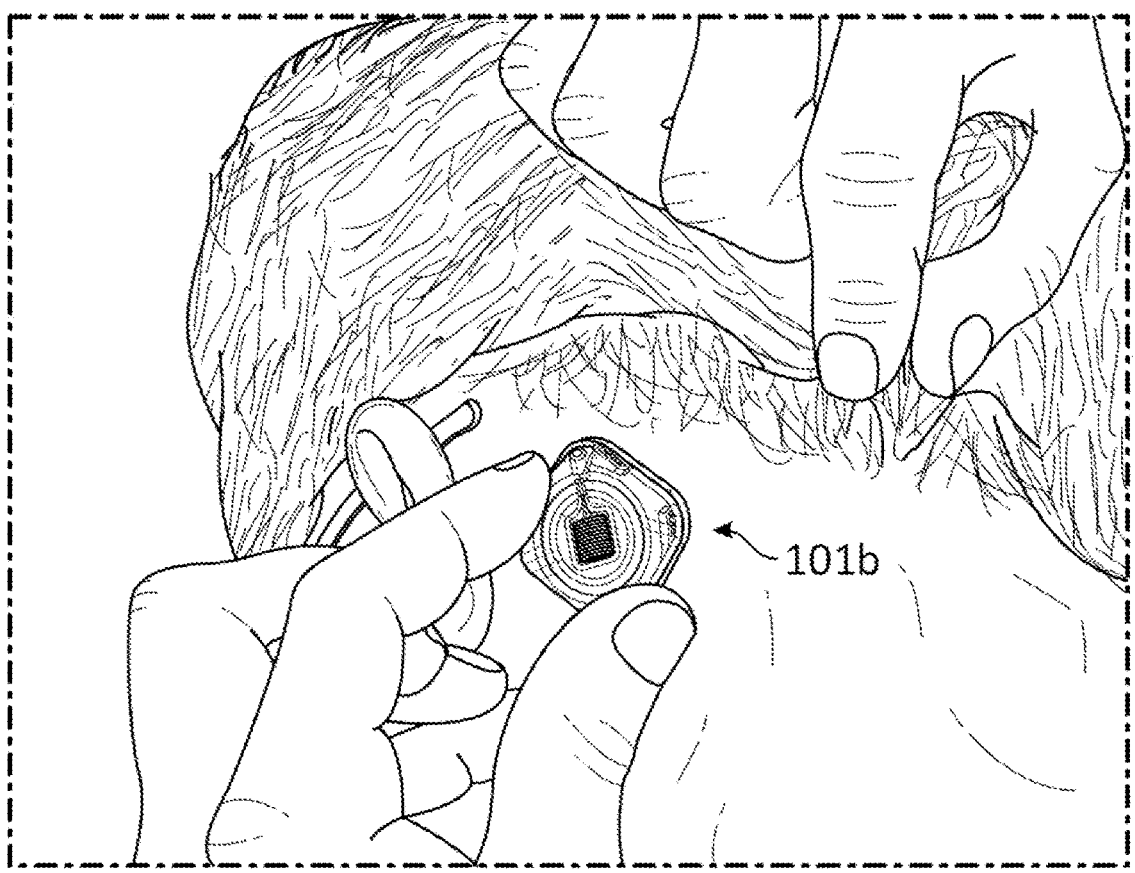
FIG. 1B illustrates an example sensor.
Figure 2:
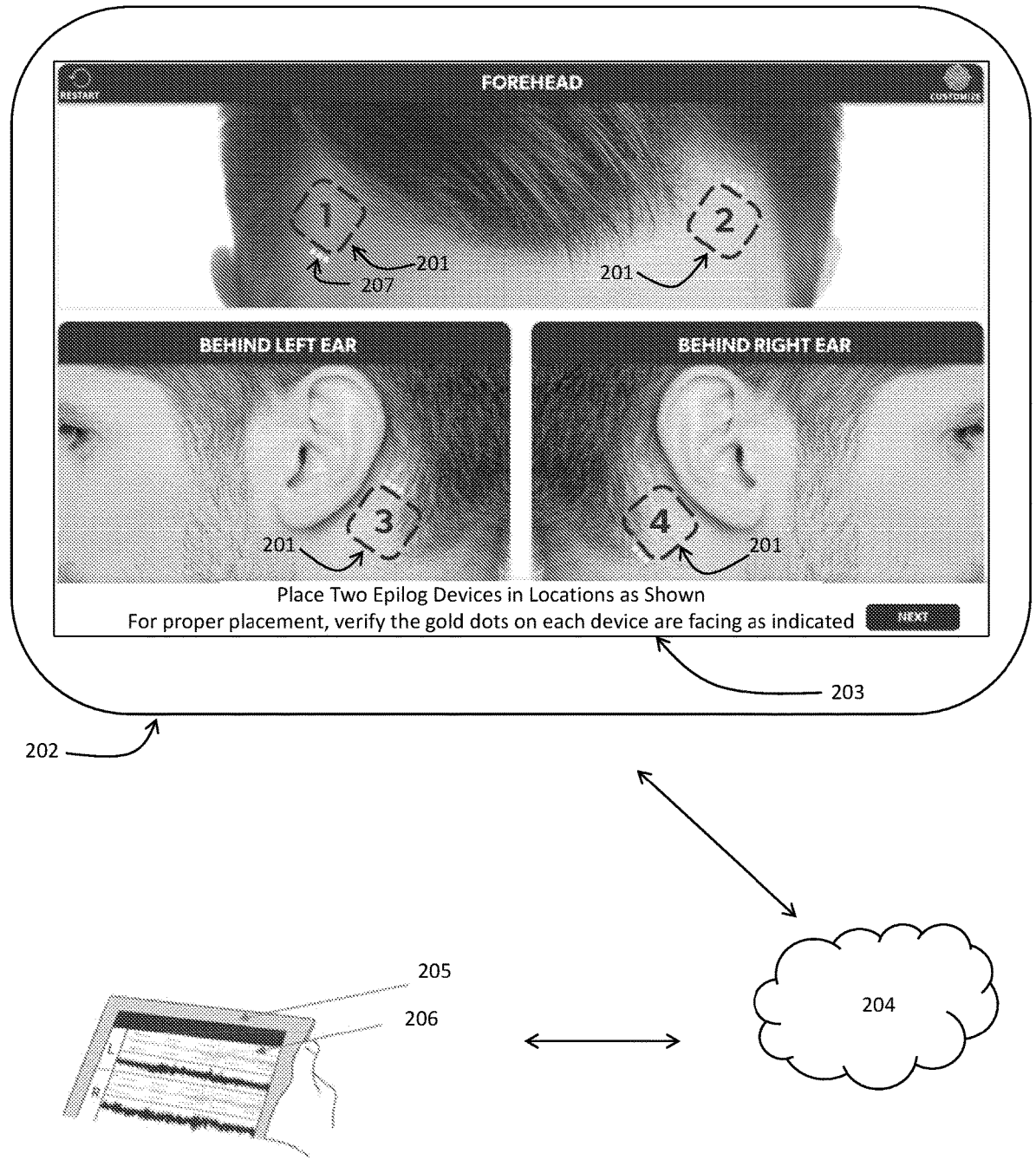
FIG. 2 illustrates an example system.

As illustrated in FIG. 1B, in an embodiment, the sensor 101b is designed to be discreet and water-resistant, allowing for continuous use in all facets of a person's normal daily life. In the example of FIG. 2, the sensor 101b may be located below the hairline in a location such as behind the ear. The placement of the sensor 101b may be aided by a prior diagnosis, e.g., following a formal evaluation using a full montage of sensors (via monitoring with a typical wired sensor array in a cap) or via refined location estimates facilitated by adjusting the location of the sensor 101b or a set of sensors over time. By choosing an appropriate placement for the sensor 101b, the usefulness of single channel EEG data is improved by locating the sensor 101b proximate to brain activity or focus of seizure activity in the brain.

By way of non-limiting example, a patient may initially receive a diagnosis of seizure activity with a location indicated, e.g., from a clinician. Thereafter, the patient may be asked to monitor for seizure activity using a sensor 101b. In an embodiment, a data source indicating a diagnosed location of seizure activity is accessed, such as an electronic medical record (EMR) or in an application that receives user input to a location map image or illustration. The location data may be supplied to the patient, e.g., via a companion mobile application that facilitates pairing and data communication between the sensor 101b and a local device. In another example, the location information is supplied to an online application that can be viewed by the user (e.g., patient or clinician). The location data may therefore be provided to the user in the form of an instruction that indicates acceptable placement(s) of the sensor(s), e.g., sensor 101b, to maximize the likelihood that a subsequent seizure will be detected using a single channel sensor, e.g., sensor 101b.

Due to the small size of the sensor 101b, for example on the order of an inch in length and width, and ½ inch in a depth dimension, the sensor 101b may be worn continuously for a period of days before it needs to be removed, e.g., for charging an on-board power source such as a rechargeable battery. This permits the capture, recording and analysis of a large amount of single channel EEG data using detection processes that identify seizures, including seizures a user wearing the sensor may not consciously know they are having, such as seizures that occur while sleeping.

The sensors 101a, 101b illustrated in FIG. 1A and FIG. 1B are suitable for use in any patient, adult, adolescent, children or newborns. A single sensor 101a, 101b may be used to facilitate more accurate recording of EEG data for real-time or later analysis. The sensor is also waterproof or water resistant, making it suitable for wear during activities where the sensor 101a, 101b may get wet. This further facilitates long-term wear and comprehensive EEG data collection for seizure diaries, seizure forecasting and seizure alerting.

A consideration in making the sensor 101a, 101b a viable, long-term wearable sensor is power consumption. An example target is approximately three days of operation without recharging the sensor 101a, 101b. To enable continued monitoring, the users may have two (or multiple) sensors 101a, 101b and will use one while the other is being recharged. Such an arrangement will allow for continuous EEG data capturing and monitoring.

To facilitate long term wear, several techniques may be employed. For example, a power consuming operation of the sensor 101a, 101b is transmitting the EEG data from the sensor 101a, 101b to another device. To reduce the power used for data communication, the sensor 101a, 101b may transmit the captured EEG data at intervals. For example, the sensor 101a, 101b can capture EEG data for a predetermined amount of time (e.g., 6 seconds) and then transmit that captured EEG data, e.g., transmit a page or pages of EEG data. By transmitting the data at intervals, the sensor 101a, 101b only needs to activate the transmission capability for a short time (e.g., 1 second). As another example, a power-efficient microprocessor may be selected for use in the sensor. For example, certain microprocessors may include a sleep processor core or capability while transmitting data by DMA to low power SRAM for data communication. This feature may significantly reduce power consumption. Further, sensors 101a, 101b may have certain components omitted, e.g., wireless radio, and may include other components, e.g., USB or other data communication element, such as near-field or RFID, in a variety of combinations, to facilitate power conservation and adequate data transfer for the given use case. In a case where a physical communication port is included, it may be covered to prevent water or contaminating element entry, such as locating it beneath a removable hydrogel or sticker that adheres the sensor 101a, 101b to the user's skin. The thickness of the sticker may be modified, e.g., the thickness of the sticker or materials thereof (e.g., hydrogel areas) may be increased to accommodate the use context, such as placement on skin that curves, whereas a thinner sticker may be used on a relatively flat surface.

The sensors 101a, 101b are suitable for use by adults, adolescents, children and neonates. In the example of FIG. 2, a system for monitoring in a clinical or emergency care setting is illustrated.

The example of FIG. 2 uses an example patient; however, this non-limiting example may be extended to other clinical or non-clinical scenarios. Seizures are common in emergency care scenarios or asphyxiated neonates (particularly within the first two days of life). Full-montage clinical EEG systems use many (eleven or more) tethered (wired) electrode leads for monitoring. These leads must be positioned by an EEG technician and can take up to 60 min to place. A reduced set (3-lead) amplitude integrated electroencephalography (aEEG) recording system provides real-time EEG from two channels along with a history of EEG activity displayed as a filtered, rectified, and averaged signal. However, electrodes are conventionally placed by a specialist. The aEEG leads are placed in the bi-parietal region of the standard 10-20 EEG system. An aEEG can be used to diagnose seizures as well as other background EEG abnormalities associated with encephalopathy. A persistently abnormal aEEG for as little as 48 hours is associated with an adverse neurodevelopmental outcome.

In FIG. 2, an embodiment is shown in which multiple single-channel sensors (collectively indicated at 201) are placed on a patient's scalp, spaced from one another to be approximately over the eyes in the bi-parietal region and behind each ear for creating an EEG montage. Alternatives are possible, for example, two sensors may be placed over roughly the bi-parietal region in the 10-20 EEG system to create three channels: (1) C3-P3, (2) C4-P4, and (3) a hybrid of C3P3-C4P4. The output of the sensors 201 is synchronized and organized by an application (as further described herein) and may be viewed both in real-time and converted, e.g., to aEEG, by software.

As with a post-diagnosis instruction, an instruction for positioning the sensors 201 may be provided using a device 202 such as a desktop computer, tablet, other hospital monitor or mobile device, which runs an application 203 and displays an instruction as a graphic indicating placement information for the sensors 201 on the patient's scalp, e.g., on the forehead, behind the ears, a combination thereof, or other or additional locations. The placement information in this case may be generalized, e.g., approximate location for seizure monitoring in patients thought to have suffered a given type of brain injury or traumatic event, or may be customized in some fashion if access to additional data is available, e.g., specific type of incident suspected for the patient or in another clinical scenario, such as for an adult or pediatric emergent care patient. By way of specific example, an embodiment may provide a graphical instruction such as that illustrated in FIG. 2, where an emergent care screening is to be conducted on a patient using four sensors, two on the forehead and two behind the ears. With this four-sensor arrangement, an embodiment may create a desired montage (as described herein), e.g., via subtracting the EEG signal from one sensor relative to another to create a 10-channel "longitudinal-transverse" montage, as further described in connection with FIG. 4B.

In the example illustrated in FIG. 2, an application 203 runs on the device 202, e.g., medical grade tablet. The application may be programmed to facilitate collecting EEG data for emergent care, although a version of the application may be used for home use in a seizure diary context. In one example, the application 203 provides instructions for EEG data collection by non-experts, such as clinicians in a local or rural hospital unaccustomed to EEG monitoring. By way of example, the application 203 may provide a graphic such as illustrated in FIG. 2 that indicates placement and orientation of four single-channel sensors 201. In some examples, the single-channel sensors 201 may be directional and keyed, such as via inclusion of a marking. In the example of FIG. 2, the graphic illustrates gold dots 207 that correspond to similar markings on the single-channel sensors 201, which allow correct orientation of the electrodes on the underside of the device (not shown) for placement on the patient's scalp. That is, a keyed device permits the user to appropriately align the single-channel sensors 201 on the patient.

The instructions and wireless single-channel sensors permit rapid collection and analysis (even remote analysis) in the field or in a clinical setting by non-experts. This avoids or reduces the need to transport the patient to another location, such as a larger hospital with conventional EEG monitoring equipment and specialists. For example, upon seizure suspicion, emergency department staff in a community hospital can place four sensors 201, as instructed by the graphic illustrated in FIG. 2, on the scalp and below hairline. The sensors begin transmitting EEG data to a tablet or other device, which may be the same device that displays the graphic, i.e., 202 in the example of FIG. 2. The tablet or other device 202 then relays the EEG data and patient information to a secure cloud server 204, e.g., running an EEG reviewing platform software. The emergency department staff then orders a neurology consult with the tertiary hospital EEG service either within or outside of their hospital network. The epileptologist on call at the tertiary hospital logs on to a mobile application 206 running on a device 205 to review the EEG in real time or substantially in real time, while also being able to use the quantitative EEG analysis features in the EEG reviewing platform. Other or additional data may be similarly provided, e.g., by other sensors or devices, such as images or video of the patient captured with a camera, heart rate, pulse oximetry, or temperature data captured by suitable devices, etc. An embodiment may provide an alert or forecast based on the EEG data, e.g., preliminary diagnoses, suggested options such as transport patient, continuation or discontinuation of pharmaceutical treatment or intervention, etc., or simply indicate areas in the EEG trace data where a seizure or other EEG abnormality is suspected.

In one example, the application 203 connects to the sensors 201 through BLE, receives the EEG data, buffers the EEG data, and transmits the EEG data over WIFI to the cloud 204, where it may be retrieved and viewed by another clinician in a remote location. For example, the EEG data may be retrieved from the cloud 204 and reviewed by a remote specialist on a medical grade tablet or other device 205. This facilitates review of the EEG data as displayed in an application 206 running on the device 205. EEG data from both sensors 201 may be synchronized, e.g., by the BLE commands from the tablet 205.

The cloud device 204 may provide a server instance running EEG-review software that allows a specialist such as a neonatologist or pediatric epileptologist to log on to a tablet 205 running a mobile application 206 to view the EEG in real-time and as aEEG. The aEEG data may include indications, such as a marking described in connection with FIG. 4A.

The general principals of the example in FIG. 2 may be extended to other scenarios. For example, in an embodiment for intensive care in pediatric and adults, two sensors, four sensors, eight sensors, or various combinations of sensors may be used. Data flow and operations are similar to the example of FIG. 2, and an adult epileptologist or pediatric epileptologist can log on to a device 205 to monitor EEG data in real-time, enabling them to make more accurate decisions faster, advising community hospital staff on appropriate care. Similarly, for a triage use case, four sensors in roughly F7, F8, TP9, and TP10, as in the example of FIG. 2, approximation of the international 10-10 system gives a total of 8 electrodes producing 10 channels of EEG, as further described in connection with FIG. 4B. In an embodiment, the EEG data obtained by various single-channel sensors may be synchronized and combined to create desired differential montages. This may be accomplished at least in part an application or software program, e.g., that determines a differential montage available (e.g., 10-10) given the number and placement of the sensors, displays this to a user, and permits a user to select a desired configuration or automatically configures the montage for the user.

In an embodiment, an application, e.g., running on device 202, visually guides a user, e.g., emergent care staff, with step-by-step visuals. This may include but is not necessarily limited to guiding the user through scanning a barcode on a patient bracelet and each sensor, placing sensor(s) on the scalp, and ensuring quality signals are being recorded and relayed, e.g., to the cloud. In some embodiments, additional or reduced data may be provided. For example, EEG data may not be shown at the point-of-care, e.g., at device 202. This may be done to accommodate emergency room staff and doctors, which may consider such data display to be a distraction. In other embodiments, such data may be displayed, e.g., in connection with an alert to a specific action such as a seizure type detection, a suggested treatment or transport option, etc. Therefore, in an embodiment, the application running on device 202 may be designed to only interact with the user when there is a problem in the form of a user alert, such as poor signal quality coming from an individual sensor or the like. These user alerts are designed to indicate, e.g., flash an LED red or blue on each sensor, to staff that interaction with the application is required to guide them through solving a problem, e.g., obtain guidance to relocate or reorient a sensor as described in connection with FIG. 6.

Collection of EEG data with one or more single-channel sensors allows EEG data to be reviewed, along with event markers (as further described herein) to quickly determine areas within the EEG data that are indicative of seizure. As further described herein, the type and nature of detection, analysis or classification the EEG data is subjected to may change depending on the use case or desired outcome. For example, for triage event marking, a model with higher false positive rate may be employed as compared to a use case in which real time seizure prediction is desired. Likewise, for in-home seizure diary use, a simple thresholding process may be suitable for producing seizure counts and markers on EEG data traces.

Figure 3:
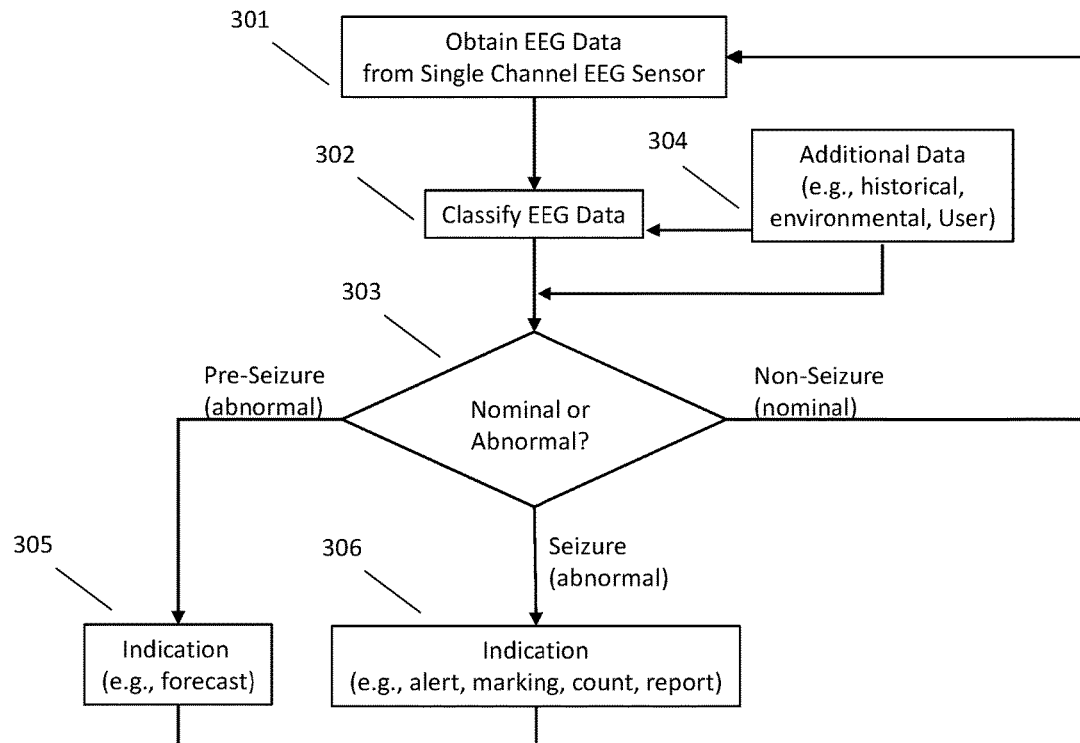
FIG. 3 illustrates an example of EEG monitoring and indicating.

Referring to FIG. 3, an example of EEG monitoring and indicating is illustrated. Often it is difficult to diagnose a seizure disorder through short-term or even long-term monitoring in an epilepsy monitoring unit with video-EEG. Furthermore, it is estimated that 20-30% of people seen in epilepsy centers are diagnosed with psychogenic non-epileptic seizures (PNES). Therefore, a mechanism to facilitate long term monitoring, e.g., home seizure monitoring, is desirable.

In an embodiment, EEG data is obtained from a single channel EEG sensor at 301. As described herein, this may be a single sensor that is placed post-diagnosis, a single sensor that is placed pre-diagnosis, or multiple sensors used in a variety of contexts. Single sensor usage may be more appropriate for in home usage, whereas multiple sensors may be more appropriate for clinical or supervised scenarios. Each such sensor provides single channel EEG data.

The single channel EEG data is classified at 302. The classification performed at 302 may be implemented using a variety of devices. For example, the classification at 302 may be performed by the sensor, at a local device communicating with the sensor via a PAN, at a remote or cloud device communicating with the sensor via a WAN, or a suitable combination of the foregoing.

The classification performed at 302 may take a variety of forms. For example, a detection model may take the form of simple thresholding to detect brain activity over a certain amount or duration for general seizure detection. One or more models may be designed to detect specific types of brain activity known to be useful in specific clinical settings, e.g., emergent care settings as described in connection with FIG. 2. For example, many signal processing techniques have been studied over the past 40 years to analyze and extract information from captured EEG data. The signal processing techniques can be used to discriminate between ictal (seizure) and inter-ictal (non-seizure) states and there are a breadth of scientific papers and studies describing various signal processing techniques that can be applied to EEG data. The most common pieces of information extracted from the EEG data are spike-wave occurrence, time-domain characteristics (e.g., range, variance, skew), frequency-domain characteristics, time-frequency-domain characteristics (e.g., wavelet decompositions), complexity measures (e.g., entropy, fractal dimension), correlative measures (e.g., cross-channel correlations), and state dynamics.

An embodiment uses machine learning techniques for use with single channel EEG data at 302. In an embodiment, a machine learning model may be trained using EEG data from one or more sensors, e.g., sensor 101a, in combination with other EEG data, such as collected via a wired or tethered EEG system. By way of example, two-second segments of inter-ictal (pre-seizure) and ictal (seizure) EEG data may be extracted from the sensor recordings and used to identify seizure occurrences, as further described in connection with FIG. 5.

In an embodiment, in identifying ictal states by classifying the EEG data at 302, correlation(s) with additional data, such as historical data (e.g., a pattern or trend, medical record information obtained from an EMR, etc.), environmental data (e.g., weather data), or a user's activity (e.g., behavioral) may be used to assist in determining the onset of seizure activity or indicating its past occurrence, as indicated at 304. For example, psychological, behavioral, and environmental cues can be identified as potential information correlative to the user's ictal (seizure) state. This additional data may optionally be used to make a classification of the EEG data or improve the confidence of an independently made classification.

By way of example, user feedback may be used to improve a seizure detecting process. Initially, an automated detection of general seizure activity may be performed at 302. If an embodiment detects general seizure activity, user supplied input may be used to improve the accuracy of the detection (e.g., with respect to time, severity or the like). For example, an input interface, such as a small button included on the sensor 101a or an input element included in a mobile application, may be used to provide an indication when a user feels that seizure activity is occurring, is about to occur or just has occurred. Likewise, an interface may allow the user to record the severity, duration, or other data regarding the event. This feedback is subjective, and it may not be desirable to use as a reliable source to determine an occurrence of seizure activity. However, user supplied data may provide insight into the user's experience of non-epileptic seizures. Therefore, it may be used to confirm a detected seizure or lack of detection. For example, repeated indications by a user that a seizure is occurring where EEG data is recorded with high quality and an automated analysis indicates no seizure may indicate that a user is experiencing something else, e.g., a non-epileptic seizure, psychological event. Conversely, such data feedback may indicate that model or threshold tuning is needed or desirable.

After the EEG data has been classified at 302, e.g., as nominal (e.g., non-seizure, pre-seizure) or abnormal (e.g., pre-seizure or seizure), an embodiment may provide outputs in the form of indications. In an embodiment EEG data, such as pre-seizure EEG data, may be classified as nominal or abnormal depending on the feature(s) being used for classification, the context (e.g., a mode may be selected where pre-seizure activity is ignored and classified as nominal in favor of a lower false positive rate, etc.), a varied threshold, etc. In an embodiment, if a seizure is detected as a result of the classification at 302, this classification may be used at 303 to provide an indication at 306 such as generating an alert (e.g., to the patient or a clinician), marking the EEG segment that triggered the detection or that is correlated with additional data, incrementing a seizure count, or forming a report.

Figure 4A:
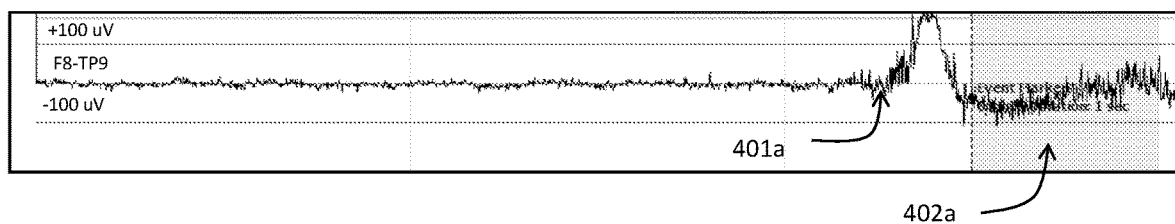
FIG. 4A and FIG. 4B illustrate example EEG data.

By way of specific example, and referring to FIG. 4A, an embodiment may provide an indication at 306 that takes the form of a marking of a segment of the EEG data as displayed in a trace 401a. The indication 402a may highlight the region of the EEG trace that triggered the classification of a seizure event. This may facilitate review by an epileptologist or another clinician. For example, color coding on the trace or text or other graphical indicator may be automatically supplied to facilitate identification of important or interesting portions of the EEG trace 401a. Additionally, or alternatively, an automated program may provide a link or position marker to navigate to this portion of the EEG trace 401a, e.g., automatically or in response to manual input. This will facilitate quick review of large amounts of EEG trace data 401a, e.g., where the patient is continuously wearing the sensor and providing a large amount of EEG data, such as over several days, to a remote clinician that wishes to quickly review important events at periodic intervals.

Figure 4B:
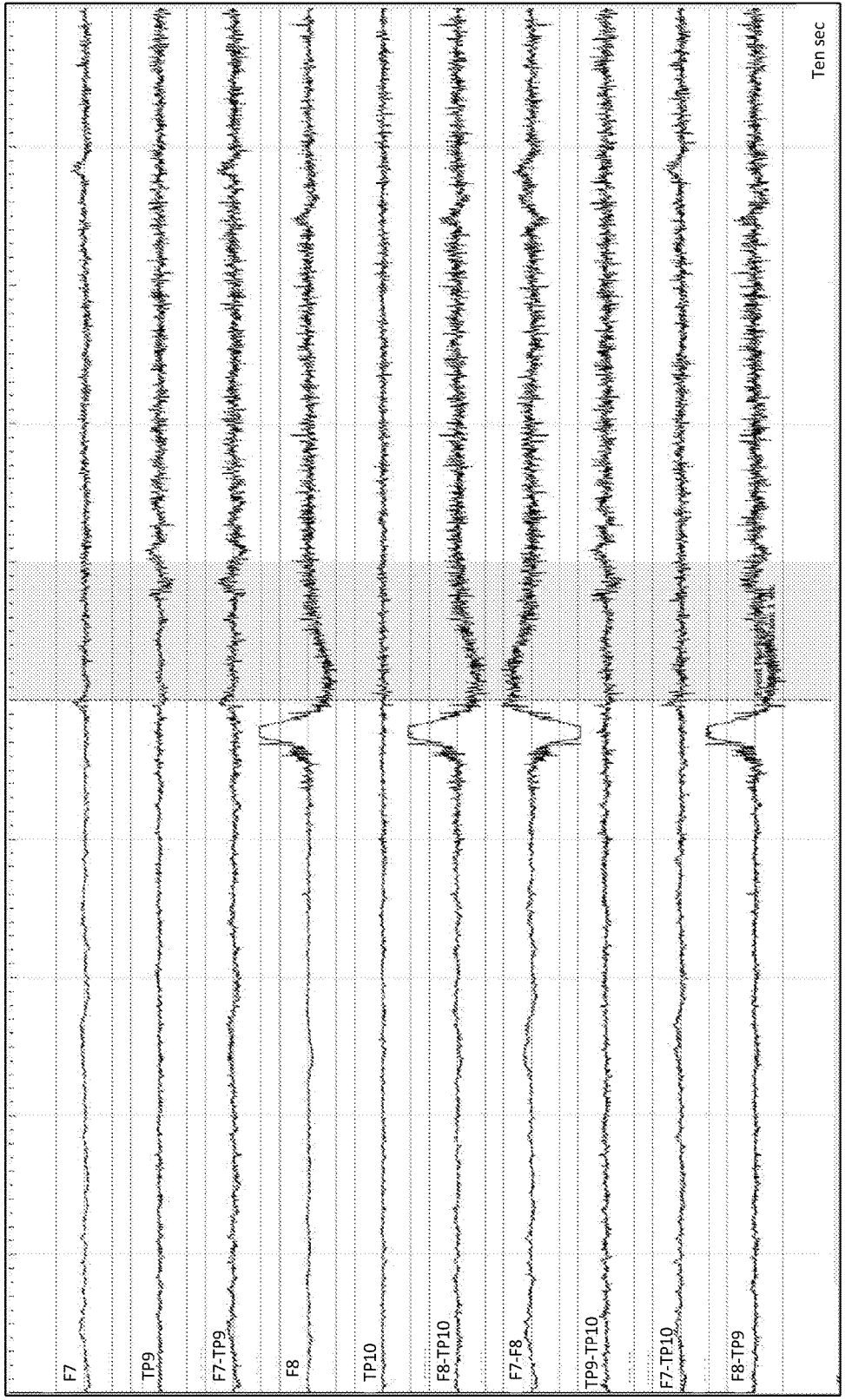

The EEG data of two or more sensors may be displayed in various manners. As illustrated in the example of FIG. 4B, individual sensor EEG trace data may be displayed as well as differential EEG data obtained via comparison to another sensor. For example, in FIG. 4B, four sensors, such as four single channel EEG sensors similar to sensor 201 have been used to record EEG data at locations approximate to F7, TP9, F8 and TP10. These locations may correspond to the forehead (front left and right) and behind the ear (left and right) locations, respectively, utilized in an emergent care setting, as described herein. In the example of FIG. 4B, the four channels of EEG trace data from the associated sensors are listed from top to bottom. Differential traces, e.g., F8-TP10, F7-F8, TP9-TP10, F7-TP10, and F8-TP9 are listed thereafter. In an embodiment, the ordering of these EEG traces may be modified, e.g., based on user preference (identified through user input such as drag and drop of the traces) or via creating more or less differential traces or individual sensor traces. By way of specific example, in a scenario where two sensors are used, the two sensor traces, e.g., F7 and F8, may be displayed, and one or more differential traces created from these sensor's readings may be displayed as well. In an embodiment, the creation or display of the traces may be automated, e.g., via an application such as described in connection with FIG. 6 and FIG. 43 determining sensor location(s) and automatically associating sensor pairs to create differential traces of interest.

Referring back to FIG. 3, where the classification at 302 results in an abnormal classification, e.g., pre-seizure, an embodiment may provide an indication at 305 in the form of a forecast or prediction. In one example, a pre-seizure classification may occur where the EEG data is abnormal, such as EEG data in which frequency and/or amplitude changes exceed threshold(s) obtained from a nominal EEG data trace, but not sufficiently so to be confidently classified as a seizure event. Similarly, a pre-seizure event may occur where the EEG data matches a known pattern that leads up to a seizure, such as a pattern indicating a characteristic frequency of change in the EEG data or a characteristic amplitude change in the EEG data, or a combination thereof, that comes before a seizure. As described in example of FIG. 5, features of EEG data that may be useful in identifying such EEG trace data may be obtained from human labeled training data. As with other classifications, this determination may be aided by reference to additional data 304, such as psychological, behavioral or environmental data.

The indication provided at 305 may include a forecast provided to the user, e.g., the wearer of the sensor. The indication provided at 305 may take the form of a real time forecast (e.g., produced within a second or two) that changes as the EEG data or other data 304 changes. The indication provided at 305 may take other forms, e.g., an hourly, daily, weekly or other time period forecast. Time period forecasts may be influenced by historical data accessed at 304, e.g., an increasing or decreasing trend in seizure frequency may assist in forming or modifying the forecast. The forecast may take a variety of forms, for example a score or a color displayed in a mobile application that relates to a likelihood of seizure during a time period, e.g., imminent, likelihood on a day, during the coming week, etc. Similarly, the forecast may take the form of a haptic, audio or visual effect produced by the sensor or a connected local device, remote device, etc. The forecast may also be provided to other or additional users, such as a clinician or another user. In the case of a forecast provided to a clinician, the forecast may include an indication of a related diagnosis, such as hypoxic ischemic encephalopathy, and a related action, such as a suggested treatment, e.g., therapeutic hypothermia, or an automated or semi-automated action, such as requesting a consultation with an on-call specialist.

Real-time or imminent seizure forecasting or prediction adds additional complexity in that discrimination must be made in a time sensitive manner, between an inter-ictal (no-seizure coming), a pre-ictal (seizure event will happen in the next X min/hours), and an ictal (seizure is occurring) states. Similar to seizure detection, information features and machine learning techniques have been widely tested and detailed in scientific literature with respect to seizure forecasting. Seizure forecasting success is often measured by sensitivity (was a warning correct that a seizure was coming and were any missed) and by either a false alarm rate per hour or by a "time-in-warning" (how often do warnings occur). Not everyone with epilepsy can identify a psychological, behavioral, or environmental seizure precipitating factor. Yet, over half of all people with epilepsy report at least one seizure precipitating factor. The number one seizure precipitating factor is emotional stress. This is followed by behavioral factors well known to trigger seizures, such as sleep deprivation and tiredness. Other behavioral factors include alcohol consumption, anti-seizure medication non-adherence, and physical exercise. Environmental factors such as time-of-day, flickering light, and weather (e.g., ambient temperature, relative humidity) have been shown to increase susceptibility to seizures.

As with seizure detection, seizure prediction may take the form of a classification performed at 302. Likewise, additional data such as historical, environmental or user provided data may be used to generate or modify the classification of the EEG data as nominal or abnormal. This data may be used to form forecasts or predictions provided at 305.

The additional data used to classify at 302 may include but is not limited to historical data (e.g., seizure trend data, etc.), environmental data (e.g., weather, stimulus data such as exposure to flickering light, etc.), and user data (e.g., behavioral data). The user data may be provided by the user directly or indirectly. For example, the user data may be input by the user directly, such as entering in self-evaluation data to a mobile application. Non-limiting examples include stress level, sleep quality rating, sleep score according to a known scale, sleep time, etc. User or other data may be obtained indirectly, e.g., from a linked health app, from a medical record, from input of another user on another device, such as a physician, or inferred from another device such as a mobile phone or smart watch providing accelerometer data, etc.

In an embodiment, an indication may take the form of a report, as indicated by way of example at 306. For example, a digital seizure diary report may be provided to the patient or clinician. Epileptologists will have a precise, quantitative record of a patient's seizure activity and that will let them know if a treatment is working, enabling them to adapt the patient's treatment more rapidly and successfully.

The improvements to a seizure detection or prediction are heavily reliant on the volume and quality of EEG data collected. Currently there exists no practical EEG database. While there are some laboratory EEG databases (e.g., MIT database), the EEG data in these databases are too clean to use for prediction as they are not representative of the quality of EEG data that will be collected in the real world. Ease of the EEG data collection will improve EEG data availability, such as via the of use of the EEG data collection sensor 101a, 101b and its minimal impact on the user's everyday routine. Hence, a feature of an embodiment is use of a single channel EEG data collection sensor 101a, 101b, accompanying EEG data analysis, and seizure prediction techniques(s). While a single channel EEG data collection may not be able to accurately identify where in the user's brain seizure activity is occurring all the time or initially, the simple detection of the occurrence of seizure activity presents a valuable tool to help users manage and treat epilepsy. As described, the location or placement of the sensor may be refined over time, e.g., in connection with a preliminary or subsequent full EEG montage, in connection with analysis of the sensor's data quality, etc. Additionally, predictive capabilities may provide users with improved quality of life as they can conduct activities with reduced anxiety that an unexpected seizure may occur.

One aspect of identifying and/or predicting seizures via classification at 302 may include discriminating between the various seizure types. For example, the absence seizure typically occurs many times a day and the electrographic signature of such a seizure is the same across all ages. Therefore, it may be comparatively easier to collect extensive EEG data and improve a seizure prediction model by machine learning to detect absence seizures. The other type of seizures may occur less frequently, such as once a month, so they may be difficult to predict accurately due to the lack of EEG data on which machine learning models can be trained. However, starting from the creation of a generalized seizure prediction model for a common seizure type, an embodiment may be expanded and refined by use of a model that covers other types of seizures, particularly as long-term wear of the sensors 101a, 101b by the users continues. This EEG data may be stored and used with permission of the users to build a database suitable for forming future seizure detection and prediction models.

Figure 5:
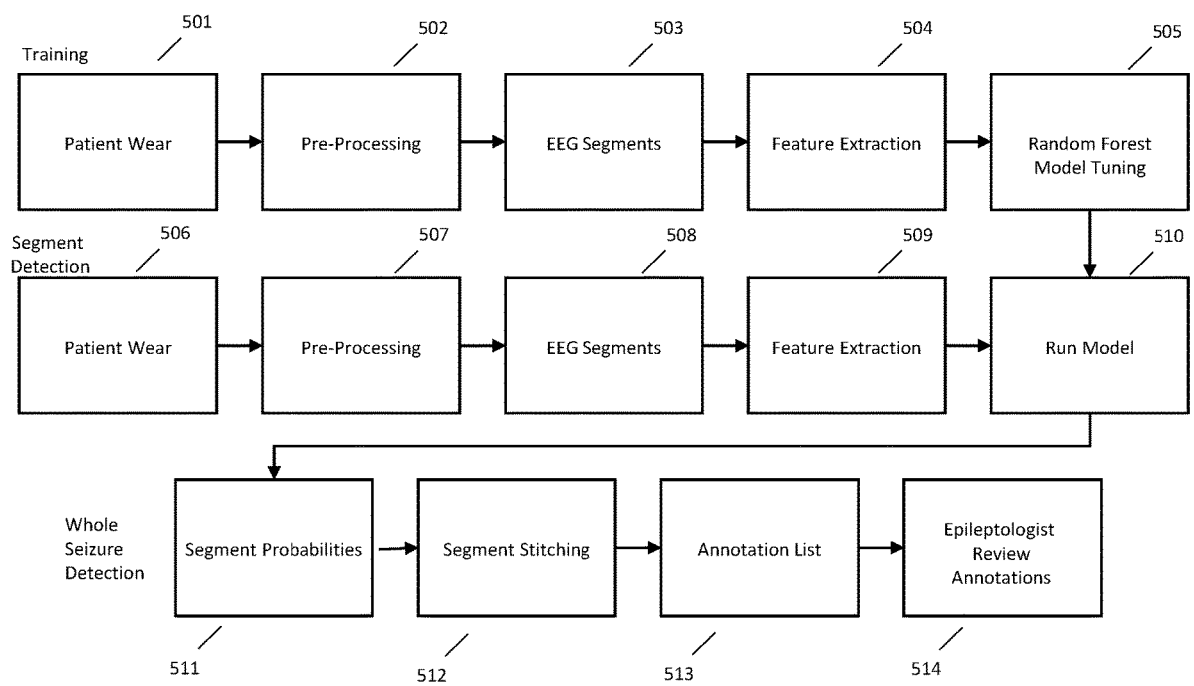
FIG. 5 illustrates an example of EEG data classification.

Turning now to FIG. 5, an example of EEG data classification is illustrated. The example classification technique shown in FIG. 5 may be used to provide a classification as part of a larger processing technique, for example that shown in FIG. 3.

In an embodiment that utilizes a machine learning process to classify the EEG data, a training phase may include processes outlined in 501-505 of FIG. 5. By way of example, as shown at 501 a patient wears a plurality of sensors, e.g., four single channel EEG sensors, such as sensor 201 of FIG. 2. In one example, four sensors 201 may be arranged on forehead and behind the ear positions, e.g., one sensor on the left forehead, one sensor on the right forehead (F7/F8), one sensor on the left behind the ear and one sensor on the right behind the ear (TP9/TP10). The sensors may be worn for a period of time to collect training EEG data, e.g., a patient may wear the sensors 201 for seven days during an Epilepsy Monitoring Unit (EMU) stay.

In one example, the training data may include both single channel EEG data collected using sensors 201 as well as EEG data collected using a normal 10-20 or 10-10 multi-channel wired EEG (wired EEG) sensor or headset as part of standard of care. That is, both the sensors 201 and the wired EEG sensor or headset may be worn by the same patient at the same time to obtain a set of EEG training data.

During an EMU stay, one or more of reviewing software and an epileptologist identifies potential seizure events in the wired EEG data record. Patients and/or family in the room may also indicate, e.g., push a button, that a seizure is occurring. An epileptologist reviews the entire multi-day wired EEG, along with the reviewing software and user provided event markers, to determine when a seizure occurred (as is conventional). An epileptologist may also review the EEG data to identify what type of seizure event occurred (as is conventional). If a seizure was focal in origin, an epileptologist may indicate which wired EEG electrodes was center of focus. An epileptologist may also indicate EEG start/stop of seizure, whether the electrographic seizure is visible on the wired EEG at locations where each sensor was placed, and electrographic obscuring artifact(s) (such as patent movement) start/stop. From this information, when a seizure should be electrographically visible (per conventional techniques) is known and this may be utilized to compare with the data obtained via the four sensors 201.

Indicated at 502, a pre-processing of raw EEG data is performed. By way of example, noise removal or filtering may be applied, such as removal of 50/60-Hz line noise, low-pass filtering to remove electromyographic (EMG) muscle activity, normalization or standardization to account for inter-patient and inter-sensor differences in the data amplitude. Other or additional signal processing conducted at 501 may include electro-ocular artifact rejection (to remove the impact of eye movement), e.g., from certain sensor placements such as F7/F8 placed sensors.

Pre-processed data is segmented into short-duration segments (for example between 0.5-10 seconds) at 503. In an embodiment, each segment is labeled, e.g., as seizure or non-seizure, based on its origin from a time previously noted as during a seizure in the patient wearing phase of 501 and if the seizure was visible at the sensor 201 location(s).

Feature Extraction is performed at 504. In an embodiment, one or more of the following features are extracted from the segmented data: time domain (min, max, mean, median, range, variance, standard deviation, skew, kurtosis); frequency domain (Fast-Fourier Transforms, EEG specific bands (s, delta, theta, alpha, beta, gamma)); time-frequency domain (wavelets); complexity domain (sample/spectral entropy, non-linear energy operator, Hjorth parameters, fractal dimensions); transforms: (principal component analysis, linear discriminant analysis); and historical (past segment values, which may be weighted).

Model tuning is performed at 505. Because the EEG sensor data is highly-imbalanced (e.g., 100:1 ratio of non-seizure segments to seizure), a subset of the EEG data may be used (e.g., 3:1 for the EEG data/model). A machine learning model, for example a random forest as shown in FIG. 5 or a support vector machine, an artificial neural network (shallow or deep), etc., is trained and tuned on the training data at 505. For example, tuning may include hyper-parameter tuning, feature relevance determination, gross-validation (e.g., using leave-one-out (LOO) methods), etc.

Metrics such as receiver operating curve (ROC) area under the curve (AUC), specificity, sensitivity, positive predictive value, false positive rate, or any combination of foregoing, may be used to determine the best model. In certain cases, e.g., where seizure detection is paramount and false positives are tolerable, e.g., in a seizure diary context, a particular model may be chosen over use in another scenario, e.g., where false positives are to be minimized, such as automated medication recommendations or providing suspected diagnoses. In an embodiment, the model employed may be exchanged or modified, e.g., by adjusting a parameter such as a probability threshold, to suit the use context. By way of example, an embodiment may adjust the model employed by offering the end user data input interfaces, such as displaying selectable elements that indicate the use context, which after selection loads a predetermined model or set of parameter(s) for the context indicated. For example, contexts such as seizure diary, real time alerting, emergent care, etc., may be indicated via selections, which loads a model or adjusts a model's parameter(s), e.g., probability threshold(s) that can be modified to adjust sensitivity, to match the context indicated. More experienced users may interface with the model parameters more directly.

Following the tuning at 505, the tuned model(s) may be saved for use in detection. For example, in steps 506-510, a model such as a previously tuned model is accessed and run on patient data, e.g., collected using one or more sensors 201 in a treatment scenario. As described herein, this may include a process of segment detection, as outlined in 506-510. By way of example, at 506 a patient, e.g., that has been previously diagnosed with a seizure disorder, wears one or more sensors 201, e.g., using a placement guided by the patient's epileptologist as to be the most likely to pick up seizure events. No wired EEG data would be recorded and the patient wears the sensor(s) 201, e.g., during everyday activities. In one example, the patient wears the sensor(s) 201 up to 24-hours a day and may do so for several days.

EEG data collected by the sensors 201 may be streamed into a remote device such as a cloud-platform, as per the example of FIG. 2. Raw sensor EEG data pre-processing is performed at 507, EEG segments are identified at 508, and feature(s) extracted at 509, which may be similar to the processes performed at 502, 503, and 504, respectively.

At 510, the unlabeled, segmented, feature set is run through the trained model, the outputs of which may be utilized in a whole seizure detection process, as for example outlined at 511-514.

In the example of FIG. 5, the outputs of the model run at 510 may include segment probabilities 511 for seizure events per segment or set of segments. In one embodiment, the output of the model run at 510 is a 0-1 likelihood that the segment occurs during a seizure event. In some embodiments, the specific type of seizure may or may not be determined, e.g., if a machine learning model tuned for a specific seizure type is employed, such as via user selection of such a model. In an embodiment, a general seizure detection model and identification process, e.g., as outlined in 510-514, is akin to a series of models with probabilities for each seizure type, combined or considered together to make a seizure/non-seizure determination.

At 512 segment stitching is performed. For example, segment probabilities are combined to create a start/stop time for a (whole) seizure event, i.e., consisting of multiple segments. This may be accomplished in many ways. By way of example, the segments may be stitched or combined together via individual segment thresholding (such as comparing frequency and amplitude EEG data changes to threshold(s) for each segment), a multi-segment thresholding and windowing process (combining or considering together multiple segments probabilities, e.g., in comparison to one or more thresholds), or integration windowing (e.g., weighted, leaky, etc.). The windows are typically as short as a few seconds (e.g., absence seizures) or up to minutes in duration (e.g., for focal seizures).

Annotations are generated, e.g., for a patient medical record or EEG trace display, for the start/stop time of the determined seizure events at 513. This annotation list data may be utilized in a variety of ways, e.g., as an indication per FIG. 3. For example, an embodiment may present an annotation list (list of segments of EEG data that are associated with a seizure or metadata for identifying such EEG data) directly to the patient through an application run on a local device, or directly to the clinician via a local or remote device (e.g., if the clinician is remote). The annotation list data may also be stored with the raw EEG trace data in a cloud-platform for clinician review.

Indicated at 514 is an epileptologist review stage. In an embodiment, clinicians may review the annotations and/or the raw EEG data and make clinical decisions. The process of epileptologist or simply user review at 514 may be influenced by the context. For example, in an embodiment, a low-threshold may be set (as described herein) that leads to many false positives. In such an embodiment, a whole seizure/no-seizure determination may or may not even be made. Rather, the annotations produced at 513 may be provided to a clinician, e.g., for more rapid review of potentially interesting EEG data, and seizure/non-seizure decisions may be made by the clinician based on this review. In other contexts, the review may be conducted by another, e.g., an at home user making a seizure diary. In this context, additional or different data may be displayed, e.g., time or location context data indicating when the potentially interesting EEG data was recorded to facilitate user review.

Figure 6:
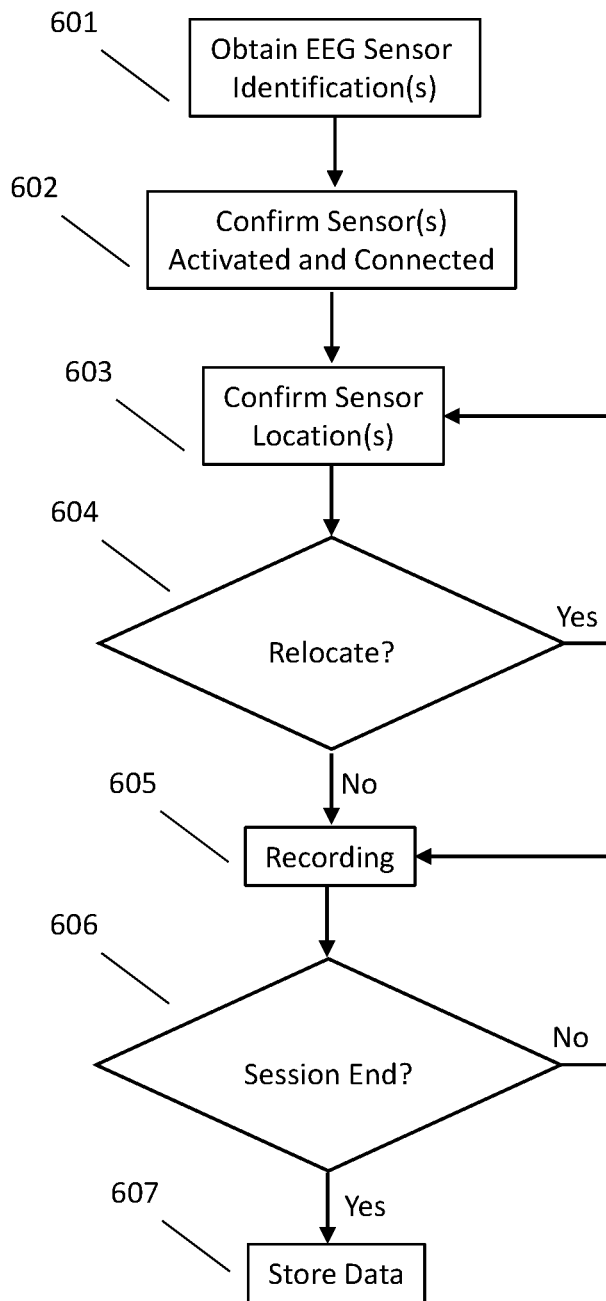
FIG. 6 illustrates an example method of EEG monitoring and indicating.
Figure 7A:
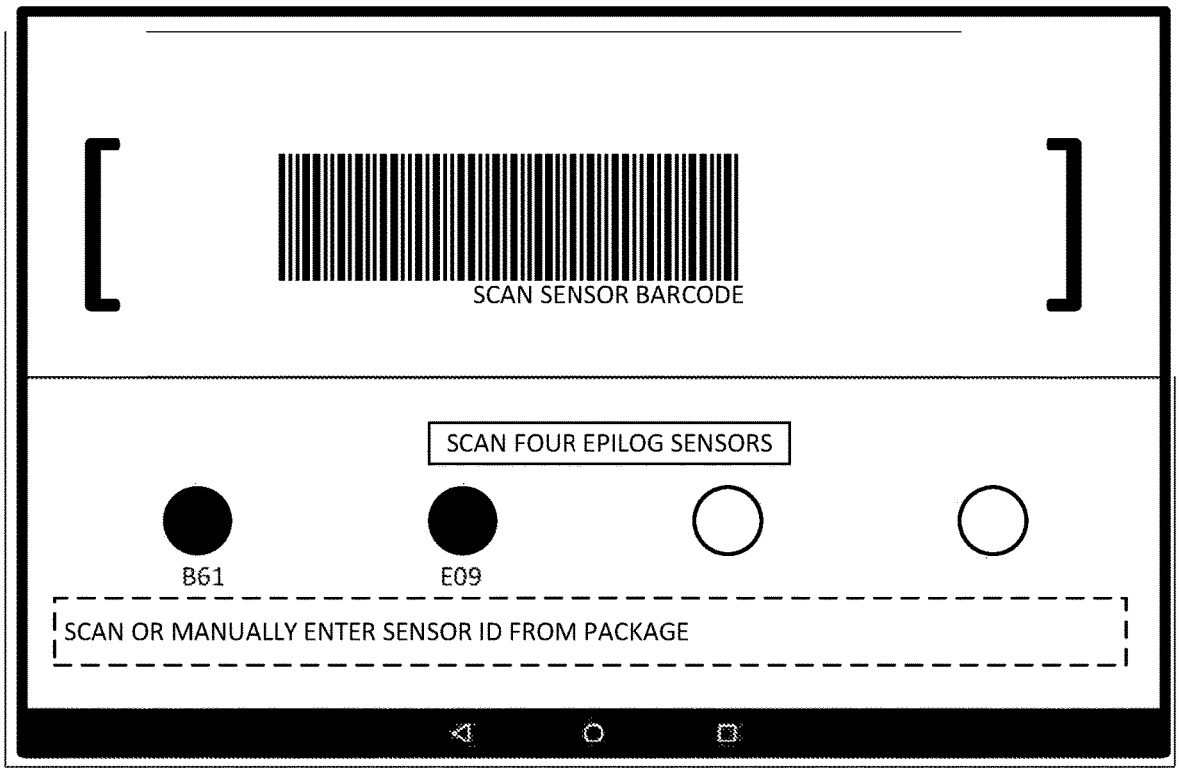
FIG. 7A and FIG. 7B illustrate example application views or screens.

Referring to FIG. 6, to facilitate use of one or more EEG sensors such as sensor 201 by non-expert users, an embodiment provides an application, such as a mobile application for use on a mobile device, that guides the user in placing the sensors and recording EEG data. By way of example, as illustrated in FIG. 6, an embodiment permits the user to easily capture sensor or patient data using the mobile device. In the example of FIG. 6, at 601 the application obtains sensor data, for example via capturing an image of a bar code, QR code, or other coded data, such as for example provided with each sensor. This permits an embodiment to automatically identify the sensor. Similarly, patient data may also be automatically or semi-automatically captured by the application. Of course, as will other data inputs described herein, the data may be entered manually. An example screen or application view of a user capturing sensor data from a bar code is provided in FIG. 7A. As illustrated in FIG. 7A, the application may capture an image of the bar code and automatically populate the display screen with the captured sensor information (e.g., an identification formed from the bar code or other captured data). The application may further indicate to the user how many sensors are to be used for the application or context. In the example of FIG. 7A, four sensor locations are indicated, two of which have been successfully identified. This assists the user in determining how many sensors are to be used in the scenario, e.g., four sensors for an emergent care scenario.

In an embodiment, an application may further display instructional steps to the user. For example, the application may display instructions for turning on or activating the sensor, pairing a sensor, which may be an automated or semi-automated routine accomplished with a user input such as a button press, confirming that a sensor is connected to the mobile device, confirming that the mobile device is connected with a remote device (e.g., cloud platform), preparing a sensor to be adhered to a patient, determining the appropriate location(s) for sensor placement on the patient, re-positioning the sensors in the application, recording data, and storing data (locally or remotely). Further, the application may include additional or alternative display capabilities, e.g., the ability to have a live video call with an expert, clinician, etc., the latter of which may assist in live or real-time troubleshooting or diagnosis contexts.

Figure 7B:
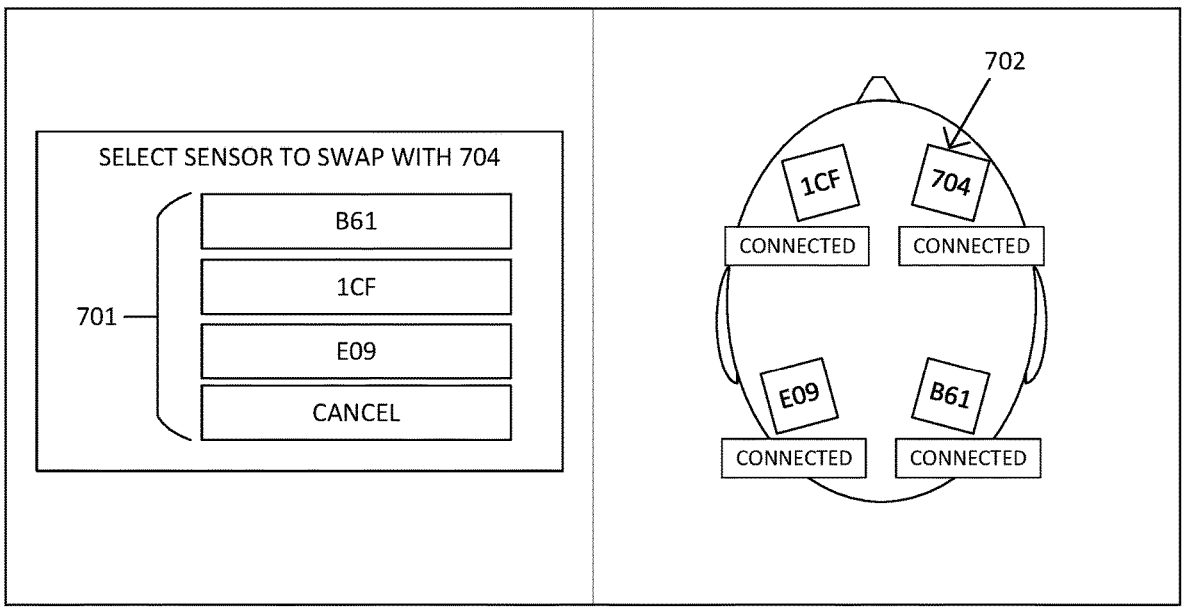

Once the user has activated and connected the sensor(s) to the mobile device running the application, this is confirmed by the application as illustrated at 602. For example, the application may display the sensor(s) in a location illustration, as indicated in FIG. 7B. This assists the user in determining if the sensor(s) are properly located on the patient for the given context and this is accurately reflected in the application view. In the example of FIG. 7B, the sensors are to be located in forehead and behind the ear positions, as illustrated. If a given sensor ID in the illustration provided by the application does not match the actual location of the physical sensor on the patient (e.g., visible on the bar code or otherwise identifiable on the physical sensor), a user may select (e.g., touch in the case of a mobile touch screen) the subject sensor icon to reassign its location in the illustration. By way of example, if sensor 704 of FIG. 7B is illustrated by the application as a right-front located sensor, but in reality, it was placed on the left-front by the user, the user may simply relocate it by interfacing with the application. This may take a variety of ways. In the example of FIG. 7B, a user may touch a selectable icon, one of which is indicated at 702 for sensor 704, to bring up a menu for swapping its position with another sensor in the array, as indicated at 701. Similarly, another mechanism such as drag and drop of the icon 702 may be used to reposition the sensor(s) in the application. This ensures that the EEG data collected by the actual sensors is known to the application, e.g., for creating differential EEG data via subtraction from another sensor location.

Referring again to FIG. 6, an embodiment may confirm that the sensor locations are appropriate at 603, following which, if no decision to relocate the sensor(s) is forthcoming, as indicated at 604, a recording session may begin, as shown at 605. At a predetermined time or based on another factor such as user selection or interface, the recording session may be concluded, as determined at 606. Thereafter, the EEG data of the session may be stored locally, remotely, or both, as indicated at 607. As described herein, during the recording at 605, other activities may be performed by an embodiment. For example, the EEG data of the sensor(s) may be analyzed locally or remotely, e.g., by a cloud platform, a remote clinician, etc.

Figure 8:
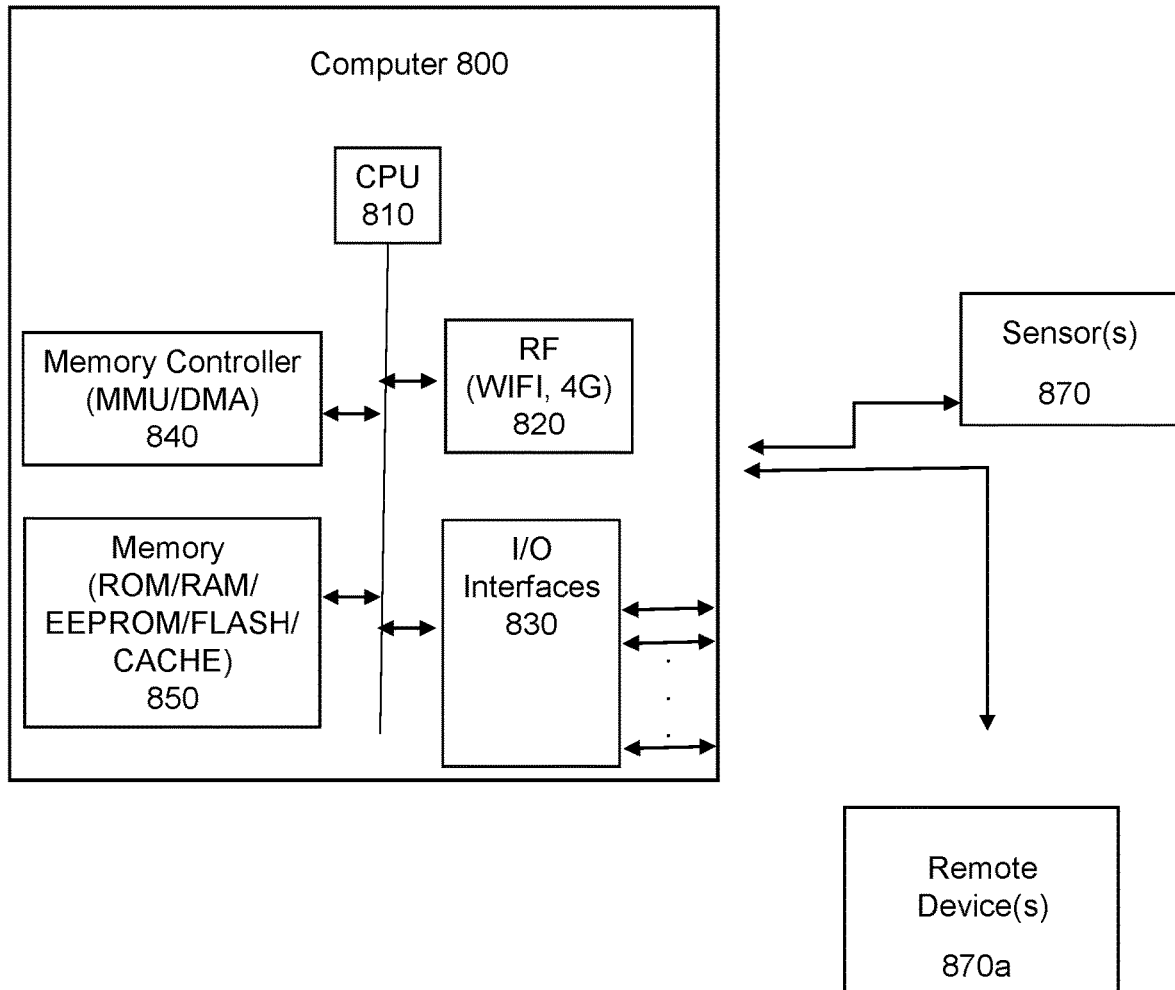
FIG. 8 illustrates an example system.

It will be readily understood that certain embodiments can be implemented using any of a wide variety of devices or combinations of devices. Referring to FIG. 8, an example system on chip (SoC) included in a computer 800 is illustrated, which may be used in implementing one or more embodiments. The SoC or similar circuitry outlined in FIG. 8 may be implemented in a variety of devices in addition to the computer 800, for example similar circuitry may be included in a sensor 870 or another device or platform 870a. In addition, circuitry other than a SoC, an example of which is provided in FIG. 8, may be utilized in one or more embodiments. The SoC of FIG. 8 includes functional blocks, as illustrated, integrated onto a single semiconductor chip to meet specific application requirements.

The central processing unit (CPU) 810, which may include one or more graphics processing units (GPUs) and/or micro-processing units (MPUs), includes an arithmetic logic unit (ALU) that performs arithmetic and logic operations, instruction decoder that decodes instructions and provides information to a timing and control unit, as well as registers for temporary data storage. The CPU 810 may comprise a single integrated circuit comprising several units, the design and arrangement of which vary according to the architecture chosen.

Computer 800 also includes a memory controller 840, e.g., comprising a direct memory access (DMA) controller to transfer data between memory 850 and hardware peripherals. Memory controller 840 includes a memory management unit (MMU) that functions to handle cache control, memory protection, and virtual memory. Computer 800 may include controllers for communication using various communication protocols (e.g., $I^2C$, USB, etc.).

Memory 850 may include a variety of memory types, volatile and nonvolatile, e.g., read only memory (ROM), random access memory (RAM), electrically erasable programmable read only memory (EEPROM), Flash memory, and cache memory. Memory 850 may include embedded programs and downloaded software, e.g., EEG processing software, etc. By way of example, and not limitation, memory 850 may also include an operating system, application programs, other program modules, and program data.

A system bus permits communication between various components of the computer 800. I/O interfaces 830 and radio frequency (RF) devices 820, e.g., WIFI and telecommunication radios, BLE devices, etc., are included to permit computer 800 to send and receive data to sensor(s) 870 or remote devices 870a using wired or wireless mechanisms. The computer 800 may operate in a networked or distributed environment using logical connections to one or more other remote computers or databases. The logical connections may include a network, such as a personal area network (PAN), a local area network (LAN) or a wide area network (WAN) but may also include other networks/buses. For example, computer 800 may communicate data with and between a sensor 870 and remote devices 870a over the Internet.

The computer 800 may therefore execute program instructions configured to store and analyze EEG data, and perform other functionality of the embodiments, as described herein. A user can interface with (for example, enter commands and information) the computer 800 through input devices, which may be connected to I/O interfaces 830. A display or other type of device may also be connected or coupled to the computer 800 via an interface selected from I/O interfaces 830.

It should be noted that the various functions described herein may be implemented using executable instructions stored in a memory, e.g., memory 850, that are transmitted to and executed by a processor, e.g., CPU 810. Computer 800 includes one or more storage devices that persistently store programs and other data. A storage device, as used herein, is a non-transitory storage medium. Some additional examples of a non-transitory storage device or medium include, but are not limited to, storage integral to computer 800, such as a hard disk or a solid-state drive, and removable storage, such as an optical disc or a memory stick.

Program code stored in a memory or storage device may be transmitted using any appropriate transmission medium, including but not limited to wireless, wireline, optical fiber, cable, RF, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on another device. In some cases, the devices may be connected through any type of connection or network, including a LAN, a WAN, a short-range wireless mechanism such as a PAN, a near-field communication mechanism, or the connection may be made through other devices (for example, through the Internet using an Internet Service Provider), using wireless connections or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device to produce a special purpose machine, such that the instructions, which execute via a processor of the device implement the functions/acts specified.

It is worth noting that while specific elements are used in the figures, and a particular ordering of elements has been illustrated, these are non-limiting examples. In certain contexts, two or more elements may be combined, an element may be split into two or more elements, or certain elements may be re-ordered or re-organized or omitted as appropriate, as the explicit illustrated examples are used only for descriptive purposes and are not to be construed as limiting.

Although illustrative example embodiments have been described herein with reference to the accompanying figures, it is to be understood that this description is not limiting, and that various other changes and modifications may be affected therein by one skilled in the art without departing from the scope or spirit of the disclosure.

What is claimed is:

1. A method for remote electroencephalogram (EEG) monitoring comprising:
    setting up at least two discrete, independent wireless sensors on a scalp of a patient to interact with a local device for initialization of the at least two discrete, independent wireless sensors and the local device, the setting up comprising displaying, by the local device, instructions for placing and orienting the at least two discrete, independent wireless sensors at particular locations on the scalp of the patient based on different positions of orientation attributes of the at least two discrete, independent wireless sensors;
    collecting single channel EEG signals by the at least two discrete, independent wireless sensors based on the setting up of the at least two discrete, independent wireless sensors;
    periodically transmitting each of at least two independent single channel EEG signals of the patient with a wireless transmitter of each of the at least two discrete, independent wireless sensors to the local device;
    buffering the at least two independent single channel EEG signals of the patient at the local device;
    transmitting the at least two independent single channel EEG signals of the patient from the local device to a remote device;
    via an application being executed on the remote device, receiving the at least two independent single channel EEG signals of the patient and synchronizing and organizing the at least two independent single channel EEG signals of the patient, whereby the at least two independent single channel EEG signals of the patient are combined to form a multi-channel montage; and
    displaying the multi-channel montage at an interactive device in communication with the remote device.

2. The method of claim 1, wherein transmitting the at least two independent single channel EEG signals of the patient comprises activating the wireless transmitter of each sensor of the at least two discrete, independent wireless sensors for 1 second.

3. The method of claim 1, further comprising displaying the at least two independent single channel EEG signals of the patient on the local device.

4. The method of claim 1, wherein the multi-channel montage is displayed in real time.

5. The method of claim 1, further comprising annotating the multi-channel montage.

6. The method of claim 5, wherein annotating the multi-channel montage comprises marking a segment associated with a possible seizure.

7. The method of claim 1, further comprising:
collecting additional data from the patient; and
transmitting the additional data with the at least two independent single channel EEG signals of the patient to the local device.

8. The method of claim 7, wherein the additional data is selected from the group consisting of images, video, heart rate, pulse oximetry, and temperature data.

9. The method of claim 1, further comprising securely storing the multi-channel montage and patient information in a cloud storage.

10. The method of claim 1, wherein the multi-channel montage comprises a differential montage.

11. The method of claim 10, wherein the differential montage comprises a longitudinal transverse montage.

12. The method of claim 1, wherein the setting up further comprises displaying, by the local device, instructions for replacing a sensor of the at least two discrete, independent wireless sensors on the scalp of the patient.

13. A system for remote electroencephalogram (EEG) monitoring of a plurality of wireless sensors, the system comprising:
at least two discrete, independent wireless sensors each configured to collect an independent single channel EEG signal from a scalp of a patient, wherein each sensor comprises two electrode contacts configured to form a single bipolar channel, a wireless transmitter configured to periodically transmit the independent single channel EEG signal, and orientation attribute;
a first non-transitory computer readable medium storing instructions that, when executed by at least one first processor, cause the at least one first processor to:
setup the at least two discrete, independent wireless sensors for placement on the scalp of the patient to interact with a local device for initialization of the at least two discrete, independent wireless sensors and the local device, the setup comprising displaying, by the local device, instructions for placing and orienting the at least two discrete, independent wireless sensors at particular locations on the scalp of the patient based on different positions of orientation attributes of the at least two discrete, independent wireless sensors;
periodically and independently receive, via a first communication protocol, each of the at least two independent single channel EEG signals collected based on the setup of the at least two discrete, independent wireless sensors;
buffer the at least two independent single channel EEG signals; and
transmit the at least two independent single channel EEG signals and patient information to at least one server via a second communication protocol configured for communication over longer distances that then first communication protocol; and
a second non-transitory computer readable medium storing instructions that, when executed by at least one second processor, cause the at least one second processor to:
receive the at least two independent single channel EEG signals and the patient information and synchronize and organize the at least two independent single channel EEG signals and the patient information, whereby the at least two independent single channel EEG signals are combined to form a multi-channel montage; and display the multi-channel montage.

14. The system of claim 13, wherein each sensor of the at least two discrete, independent wireless sensors is water-resistant.

15. The system of claim 13, wherein the instructions stored on the second non-transitory computer readable medium further cause the at least one second processor to display the at least two independent single channel EEG signals with annotations.

16. The system of claim 15, wherein the annotations comprise marking a segment associated with a possible seizure.

17. The system of claim 13, further comprising an additional sensor configured to record additional data from the patient, wherein the instructions stored on the second non-transitory computer readable medium cause the at least one first processor to transmit the additional data with the at least two independent single channel EEG signals.

18. The system of claim 17, wherein the additional data is selected from the group consisting of images, video, heart rate, pulse oximetry, and temperature data.

19. The system of claim 13, wherein the multi-channel montage is displayed in real time.

20. The system of claim 13, wherein the wireless transmitter of each sensor of the at least two discrete, independent wireless sensors is configured to be activated for 1 second.

21. The system of claim 13, wherein the setup up further comprises displaying, by the local device, instructions for replacing a sensor of the at least two discrete, independent wireless sensors configured to be positioned on the scalp of the patient.

* * * * *

UNITED STATES PATENT AND TRADEMARK OFFICE
CERTIFICATE OF CORRECTION

PATENT NO. : 12,048,554 B2
APPLICATION NO. : 17/861080
DATED : July 30, 2024
INVENTOR(S) : Michael K. Elwood et al.

Page 1 of 1

It is certified that error appears in the above-identified patent and that said Letters Patent is hereby corrected as shown below:

On the Title Page

Column 1 (Related U.S. Application Data), Line 1, delete "17/013,811," and insert -- 17/019,811, --.

In the Specification

Column 10, Line 21, delete "43" and insert -- 4B --.

Column 11, Line 60, delete "the of" and insert -- the --.

Column 13, Line 42, delete "gross" and insert -- cross --.

In the Claims

Column 20, Line 43 (approx.), Claim 21, delete "setup up" and insert -- setup --.

Signed and Sealed this
Eleventh Day of March, 2025

Coke Morgan Stewart
*Acting Director of the United States Patent and Trademark Office*